United States Patent [19]
Modderman et al.

[11] Patent Number: 5,303,590
[45] Date of Patent: Apr. 19, 1994

[54] METHOD OF AND AN APPARATUS FOR FREQUENCY SELECTIVE ULTRASONIC INSPECTION OF MULTI-LAYERED STRUCTURES

[75] Inventors: Theodorus M. Modderman, Heemstede; Wiebe F. Pronker, Roelofarendsveen, both of Netherlands

[73] Assignee: Fokker Aircraft, B.V., Schiphol-Oost, Netherlands

[21] Appl. No.: 889,112

[22] Filed: May 27, 1992

[51] Int. Cl.$^5$ .................... G01N 29/06; G01N 29/08; G01N 29/10
[52] U.S. Cl. ...................... 73/588; 73/602; 73/620; 73/629
[58] Field of Search ............. 73/579, 582, 588, 602, 73/629, 630, 620

[56] References Cited

U.S. PATENT DOCUMENTS

| | | | |
|---|---|---|---|
| 3,485,087 | 12/1969 | Brech. | |
| 4,215,583 | 8/1980 | Botsco | 73/582 |
| 4,428,235 | 1/1984 | Sugiyama | 73/582 |
| 4,457,174 | 7/1984 | Bar-Cohen | 73/598 |
| 4,825,423 | 4/1989 | Yamanaka | 73/598 |
| 4,953,405 | 9/1990 | Hara | 73/602 |
| 5,088,327 | 2/1992 | Gammell | 73/588 |

OTHER PUBLICATIONS

"Principles and Application of Ultrasonic Spectroscopy in NDE of Adhesive Bonds" by F. H. Chang, P. L. Flynn, D. E. Gordon, and J. R. Bell; IEEE Transactions on Sonics and Ultrasonics, vol. SU-23, No. 5, Sep. 1976 (pp. 334–338).

"Ultrasonic scanning and spectrum analysis for inspection of bond efficiency of metal-to-metal structural adhesive joints" by G. Biggiero, G. Cannella, and A. Moschini (NDT International) Apr. 1983, pp. 67–73.

"Ultrasonic Procedures for Predicting Adhesive Bond Strength" by Joseph L. Rose and Paul A. Meyer (Materials Evaluation) Jun. 1973 pp. 109–114.

Primary Examiner—Hezron E. Williams
Assistant Examiner—Rose M. Finley
Attorney, Agent, or Firm—Handal & Morofsky

[57] ABSTRACT

A method of an apparatus for ultrasonic inspection of multi-layered structures having acoustic transmission (I, III, V and VII) and reflection (II, IV, VI and VIII) frequency bands. Variations in one or more parameters of specific layers are largely restricted to specific frequency bands of said layers. By analyzing transmitted or reflected signals with respect to the frequency bands of the structure, interpretation of signals due to parameter variations as caused by voids, inclusions or delaminations can be effectively eliminated. The method is preferably used for the inspection of laminated structures consisting of metal layers bonded by fibre reinforced resin layers.

20 Claims, 4 Drawing Sheets

METHOD OF AND AN APPARATUS FOR FREQUENCY SELECTIVE ULTRASONIC INSPECTION OF MULTI-LAYERED STRUCTURES

FIELD OF THE INVENTION

The present invention relates to a method of an apparatus for ultrasonic inspection of multi-layered structures having acoustic transmission and reflection frequency bands, in particular for the detection of flaws in such structures.

BACKGROUND OF THE INVENTION

Ultrasonic inspection consists of subjecting a structure to ultrasonic signals, i.e. signals having a frequency above approximately 20 kHz up to approximately 25 MHz, and receiving ultrasonic signals transmitted or reflected by said structure. The transmission or reflection of ultrasonic signals by a material provides information about its structural properties, such as thickness and flaws. Flaws, such as voids, inclusions and delaminations in case of a laminated structure, are areas with different ultrasonic transmission properties. Accordingly, transmitted or reflected signals from an area of a structure having a defect differ from the signals transmitted or reflected from areas of the structure having no defect.

British patent application 2,204,690 discloses an ultrasonic method of testing the strength of a bonded joint by mutually comparing signals received from different areas of a structure under inspection. In order to separate the transmitted signals from the reflected signals or to filter out all reflected signals from positions or interfaces other than those from the joint under examination, the received signals are subjected to a first time-gating operation. The signals are subjected to a further time-gating operation for smoothening and integration purposes.

During the ultrasonic inspection of panels of ARALL (trademark), some remarkable phenomena occurred. ARALL is a laminated material consisting of relatively thin aluminum layers bonded together with a fibre reinforced resin. The material is usually fabricated in flat panels with two to six aluminum layers and one to five fibre reinforced resin layers, in particular aramide fibres, in the present specification called fibre layers. During production of the material, several types of defects can arise, the most important of which are delaminations, porous bond lines and unintended inclusions within the bond lines.

When subjecting a sample of ARALL to ultrasonic signals, areas with a relatively low transmission coefficient at one frequency showed an increased transmission at another frequency. Furthermore, areas were found with reduced transmission properties while flaws such as voids, delaminations and inclusions were absent, following microscopic examination of said areas. It was found that these effects appeared to be frequency related.

After studying the transmission and reflection properties of ARALL in the frequency domain, it was found that only within certain frequency bands ultrasound is nearly unattenuated transmitted, whereas it is totally or partly reflected in other frequency bands. This behavior can be explained in that ultrasonic signals transmitted by one layer or a combination of layers can be reflected by other layers. Multiple reflections in one layer or a combination of layers can give rise to destructive and to constructive interferences, leading to transmission and reflection bands.

Thus a multi-layer structure has been found to have alternating ultrasonic transmission frequency bands comprising relatively higher transmissivity frequency bands having a low reflectivity separated by relatively lower transmissivity frequency bands having a high reflectivity. The term "transmission band" is used herein to refer to such a higher transmissivity ultrasonic frequency band.

Physically, ARALL can be regarded as a complex (acoustical) filter. The order of the filter increases with the number of layers. As long as the layer parameters, such as layer thicknesses, the densities of the layer materials and the acoustic velocity in each layer are exactly equal among all aluminum and among all fibre layers, the filter behaves in a regular manner; i.e. the position of transmission and reflection frequency bands is determined by the actual parameter values (layer thickness and density, etc).

However, when one or more of said layer parameters vary from layer to layer for a given location, the frequency characteristics of the structure become more complex.

Accordingly, apart from attenuation or scattering due to defects such as voids, inclusions and delaminations, variations in the layer parameters of the ARALL laminates influence the transmitted and reflected signals, with the risk of misinterpretation of such transmitted and reflected signals as being caused by voids, delaminations, inclusions, etc. in the laminate.

OBJECTS OF THE INVENTIONS

The present invention has now for its object to provide an improved method of ultrasonic inspection of a multi-layered structure which method avoids interpretation of transmitted or reflected signals due to variations in layer parameters being mistakenly detected as flaws, such as voids, delaminations or inclusions.

In this specification, the term multi-layered structure is used for layered materials comprising layers of at least two materials having different acoustic properties, i.e. laminated structures, bonded structures, embedded layers etc.

Another object of the invention is to provide an apparatus for carrying out the improved ultrasonic inspection method.

SUMMARY OF THE INVENTION

These objects and others which will become apparent hereinafter are obtained in accordance with the present invention, by analyzing transmitted or reflected ultrasonic signals by a multi-layered structure under inspection with respect to the acoustic frequency bands of said structure.

It can be shown that the transmission and reflection frequency bands of a multi-layered laminated structure, such as ARALL or GLARE (trademark), which is comparable in construction to ARALL except in that the aramide fibres are replaced by glass fibres, are determined by their layer parameters. For a structure such as ARALL, there are specific transmission frequency bands relating to the fibre layers and specific transmission frequency bands relating to the aluminum layers. Variations in the layer parameters of one or more layers show a dominant influence on specific transmission frequency bands.

For example, variations in the thicknesses of the fibre layers (aramide, glass, etc.) lead to variations in the magnitude of the transmission coefficient in the transmission frequency bands relating to said fibre layers.

Generally, the more the acoustic properties of the different materials in a multi-layered structure differ one from another, the less the mutual influence on their specific acoustic transmission frequency bands will be.

Accordingly, by frequency band selective analysis of the transmitted or reflected signals, influences on said signals due to variations in the layer parameters of a multi-layered structure under inspection, such as variations in the thickness of individual layers, can be adequately detected and/or eliminated.

In an embodiment of the method according to the invention, the structure is subjected to ultrasonic signals having a frequency spectrum covering at least one frequency band of said structure, the transmitted or reflected signals being frequency band selective filtered before analyzing By filtering the transmitted or reflected signals in the frequency domain, the part of the transmitted or reflected signals relating to variations in structural parameters can be effectively filtered out.

In another embodiment of the method according to the invention, the structure is subjected to ultrasonic signals having a frequency spectrum limited to a frequency band of said structure. By suitable shaping of the ultrasonic signals in the time domain, a frequency limited spectrum can be obtained. By choosing said frequency spectrum to be within a specific frequency band of the structure, interference of transmitted or reflected signals due to variations in structural parameters of a laminate under inspection can be eliminated.

In a yet further embodiment of the method according to the invention, the transmitted or reflected signals within at least one specific frequency band of the structure are analyzed. In case of ARALL or GLARE, for example, by analyzing signals within a specific frequency band of the structure, there will be virtually no interference of the signals by variations of, for example, the thickness of one or more of the fibre layers of the laminated structure. Accordingly, deviations of the signals within that frequency band must be caused by defects in the structure, such as voids, delaminations, inclusions in the epoxy resin layers etc.

For ARALL or GLARE, the thickness of the individual fibre layers is the parameter most likely to vary over the laminates, because the thickness of such layers is constituted during the curing process. The other parameters, i.e. density and ultrasonic velocity will vary less if proper curing takes place.

The plate thickness for the aluminum layers is very constant and can be checked before production of the laminates. The thickness of the aluminum plates will not change during fabrication of the laminated structure. Also, density of the aluminum layers and ultrasonic velocity will not vary significantly from layer to layer. The total plate thickness is also controlled during manufacturing.

Because the thickness variations in, for example, the aluminum layers of ARALL are in most practical cases negligable, the frequency bands relating to these aluminum layers are generally not or virtually not affected. Accordingly, it is also possible to singly analyze transmitted or reflected signals occurring in a transmission band relating to said aluminum layers.

The choice for a particular frequency band or frequency bands may be determined by the type of flaw to be detected. For example, delaminations can be detected with relatively low frequencies, whereas porosities are more sensitively detected with ultrasonic signals of higher frequencies.

Transmitted or reflected signals due to flaws in a structure under inspection, the frequency content of which is within a given frequency band, can be evaluated, in another embodiment of the method according to the invention, by comparatively analyzing the transmitted or reflected signals within at least two different frequency bands. For example the signals in a transmission band of the fibre layers and the signals in a transmission band of the aluminum layers in case of ARALL or GLARE are mutually compared. Thickness variations of the fibre layers will show nearly no effect in a transmission band related to the aluminum layers, whereas transmitted or reflected signals due to flaws will have a significant effect within both transmission bands.

The transmission frequency bands for ARALL, for example, consist in fact of frequency ranges, wherein the transmission and reflection properties of the structure vary in a peak type manner. The number of peaks in such a transmission band is determined by the number of layers of one type, for example the aramide fibre reinforced resin layers. In, for example, a 6/5 ARALL laminate, i.e. a structure having six aluminum layers and five aramide fibre reinforced resin layers, the transmission bands determined by the fibre layers consist of five peaks, whereas the transmission bands determined by the aluminum layers having six peaks. Accordingly, by counting the number of peaks in the transmission bands, the layer composition of a structure under inspection can be determined.

It can be shown that the height and position of the peaks of the transmission coefficient varies with the thickness of a specific layer. Accordingly by analyzing the height and/or the position of the transmission coefficient peaks, information about the layer thicknesses can be gained.

In a preferred embodiment of the method according to the invention, the structure is subjected to ultrasonic pulses, the variable to be analyzed being the peak amplitude and/or energy content of transmitted and/or reflected signals in the time domain. By measuring the peak amplitude or the energy content, a qualitative impression about the structure under inspection can be obtained.

Besides amplitude and energy content measurements, other variables such as phase and frequency shifts, time delays etc. may be analyzed for obtaining information about the structure under examination.

Whenever the transmission and reflection frequency bands of a multi-layered structure under inspection are not known, these can be calculated, in a still further method according to the invention, from the layer thicknesses, the densities of the layer materials and/or the acoustic velocity in each layer, using a computer programmed multi-layered transfer function. Transfer functions for multi-layered structures can be found in many physical text books, for example "Waves in layered media", Second Edition, by L. M. Brekhovskikh, Applied Mathematics and Mechanics, No. 16. Translated by Robert T. Beyer, Academic Press Inc., 1980.

Inspection of a structure is performed with a scan. There can be distinguished three kinds of scans. The so-called A-scan is a single point measurement, the B-scan is a series of measurements on a line, whereas the C-scan is a series of measurements on a plane of the structure. Obviously, the C-scan provides information about the structure as a whole. In most practical cases this information consists of amplitude values of the transmitted signals. The results are displayed in a two dimensional form, i.e. on a videomonitor or a paperchart graph. In this manner it is easy to trace low amplitude areas. A low amplitude value often indicates an irregularity in the scanned laminate. By digitizing the measured signals, using A/D-conversion, the analyses of said signals can be performed in a digital manner using a suitable programmed computer device.

The invention relates further to an apparatus for ultrasonic inspection of a multi-layered structure having transmission and reflection frequency bands, comprising a transducer for emitting ultrasonic signals to said structure and for receiving signals transmitted or reflected by said structure, and means for analyzing at least one variable of said transmitted or reflected signals.

In a first embodiment, means are provided for filtering transmitted or reflected ultrasonic signals adapted to at least one frequency band of the structure to be inspected. Said filtering means may comprise band pass filters, centered around a fixed frequency or adjustable band pass filters.

In a second embodiment, the frequency selective measurement of transmitted or reflected signals is achieved by means for emitting ultrasonic signals having a frequency spectrum adapted to a frequency band of the structure to be inspected. Using, for example, computer means, a particular form of a pulse signal in the time domain can be composed, having the desired frequency spectrum. This is a well-known technique for persons skilled in the art, and can be found in textbooks dealing with the so-called Fourier-transforms. In this second embodiment no filtering means are required at the receiver side, avoiding phase interactions with the transmitted or reflected signals.

However, it is nevertheless possible to have an apparatus combining both measurements, i.e. filtering at the receiver side and pulse shaping at the transmitter side. This in order to avoid interferences of the reflected signals by variations in the layer parameters of the laminated structure to be inspected as much as possible.

In a further embodiment of the apparatus according to the invention, the signals are ultrasonic pulses, and the means for analyzing the transmitted or reflected signals comprise means for measuring the peak amplitude and/or the energy content of the transmitted or reflected signals in the time domain. Peak amplitude or energy content measurement is relatively easy to perform, also in a digital manner, and gives a qualitative impression of the structure under inspection.

In a yet further embodiment of the apparatus according to the invention, comparator means may be provided for comparing transmitted or reflected signals within several frequency bands of a structure to be inspected. Said comparison can be performed in a digital manner.

For scanning several locations of a structure, the apparatus may comprise means for scanning along a line or a plane of the structure. These means may be comprised of means for moving a single transducer over a surface to be inspected or may comprise an array of transducers which can be selectively excited, for example.

BRIEF DESCRIPTION OF THE DRAWINGS.

The above and other objects, features and advantages of the present invention will become more readily apparent from the following description, reference being made to the accompanying drawings in which:

FIG. 2a, b illustrate schematically two different manners of ultrasonic inspection.

DETAILED DESCRIPTION OF THE INVENTION

Figure 1:
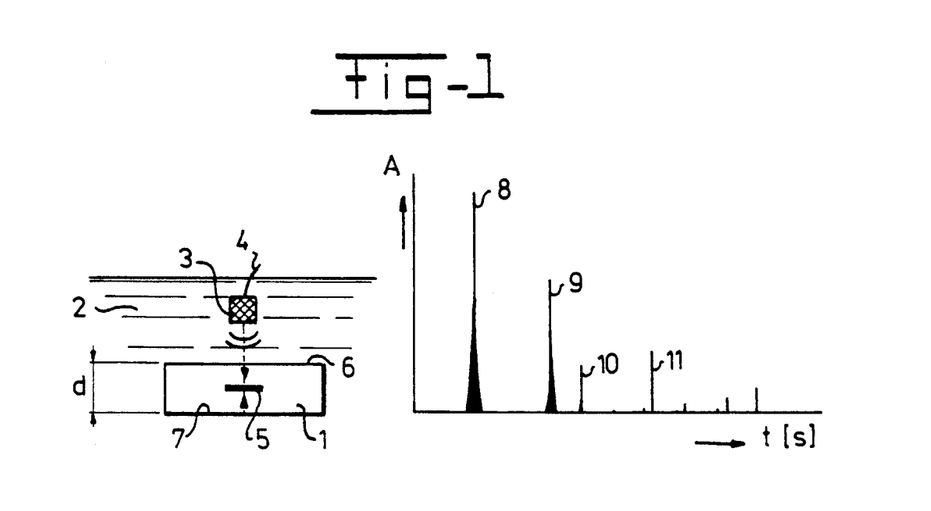
FIG. 1 illustrates in a schematic manner the ultrasonic inspection of a material, as well as transmitted and reflected signals.

FIG. 1 illustrates the ultrasonic inspection of a sample 1, immersed in water 2 as a coupling medium for guiding the ultrasonic signals produced by the transducer 3 to the sample 1 and for guiding signals from the sample 1 to the transducer 3. Instead of water 2 an other suitable fluidum may be provided as coupling medium. Instead of immersing the sample in a fluid, said fluid may be squirted. The means for energizing the transducer 3 and analyzing the signals received by said transducer 3, connected to signal cable 4, are not shown. It is supposed that the sample 1 has an inner crack 5.

In the right-hand side of FIG. 1, the amplitude A of the ultrasonic signals emitted to and received from the sample 1 are graphically illustrated with respect to the time t. The sample 1 is subjected to an ultrasonic pulse 8.

The signal received first in time after said pulse 8 is an echo signal 9 from the front wall 6 of the sample 1. The following smaller pulse 10 is due to the crack 5, while the next following pulse 11 is caused by reflection at the backwall 7 of the sample 1. Due to internal reflections in the sample 1, several other small reflection signals are received. Because said graph is for illustrative purposes only, no specific values of the amplitude A and time t are indicated. The time between, for example, the front wall echo pulse 9 and the backwall echo pulse 11 is determined by the thickness d of the sample 1 and the velocity v of ultrasound in said sample 1. The density $\rho$ of the material of said sample 1 determines, inter alia, the pulse height.

Figure 2:
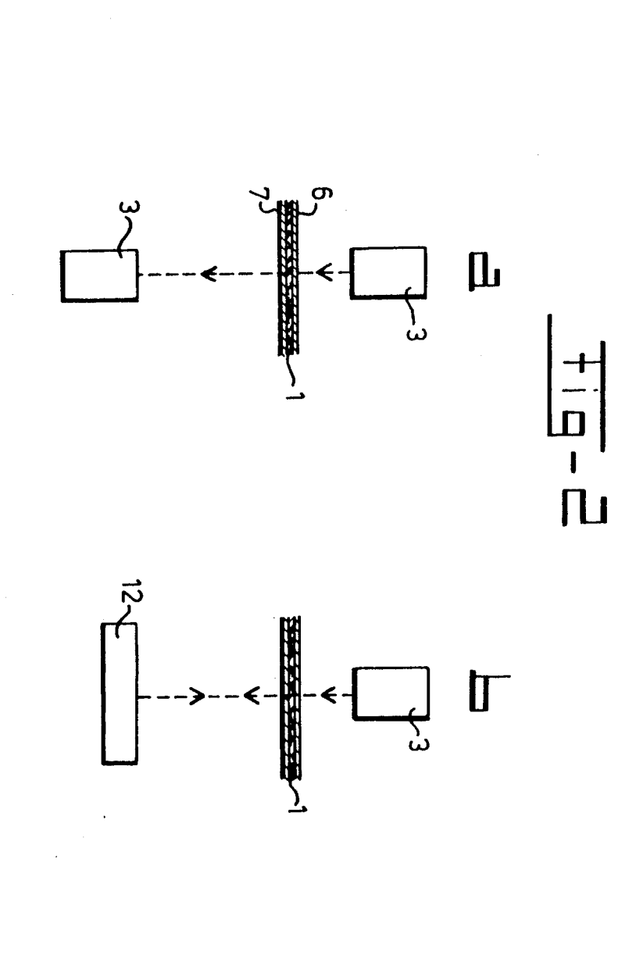

Transmitted signals can be generated in two different ways, as illustrated in FIGS. 2a, b. In FIG. 2a the so-called single type transmission is shown. After transmitting an ultrasonic pulse by the upper transducer 3 facing the frontwall 6 of the sample 1, the ultrasonic signal will pass through the sample 1 and is received by a further, lower transducer 3 facing the backwall 7 of the sample 1. The path of the ultrasonic signal is schematically illustrated by dashed arrows.

FIG. 2b illustrates the so-called double type transmission. After passing the sample 1, an ultrasonic pulse from transducer 3 is reflected by a plate 12 of for example glass, and travels back to the transducer, as illustrated with dashed arrows. In this case the sample 1 is passed twice by a transmitted pulse.

The resolution of an ultrasonic inspection is limited by the wavelength. Relatively small wavelengths provide more detailed information. Extremely high frequencies are not useful. The absorption by the material and the coupling medium becomes too high for reliable results. A frequency range of 0.5 to 25 MHz is normally used for ultrasonic inspection.

Figure 3:
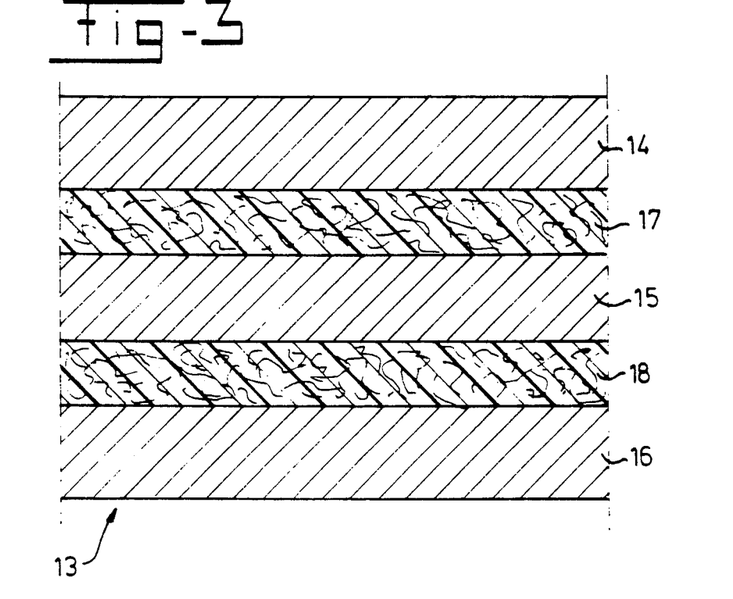
FIG. 3 shows a cross-section through an ARALL laminate, consisting of three aluminum layers bonded by two aramide fibre reinforced resin layers.

FIG. 3 shows partly a cross-section of a so-called standard 3/2 ARALL laminate 13 consisting of three layers of aluminum 14, 15, 16 having a thickness of 0.3 mm, bonded by two aramide fibre reinforced resin layers 17, 18 having a thickness of 0.2 mm.

After studying the frequency characteristics of such an ARALL laminate 13, it has been found that it behaves like a complex acoustical filter.

Figure 4:
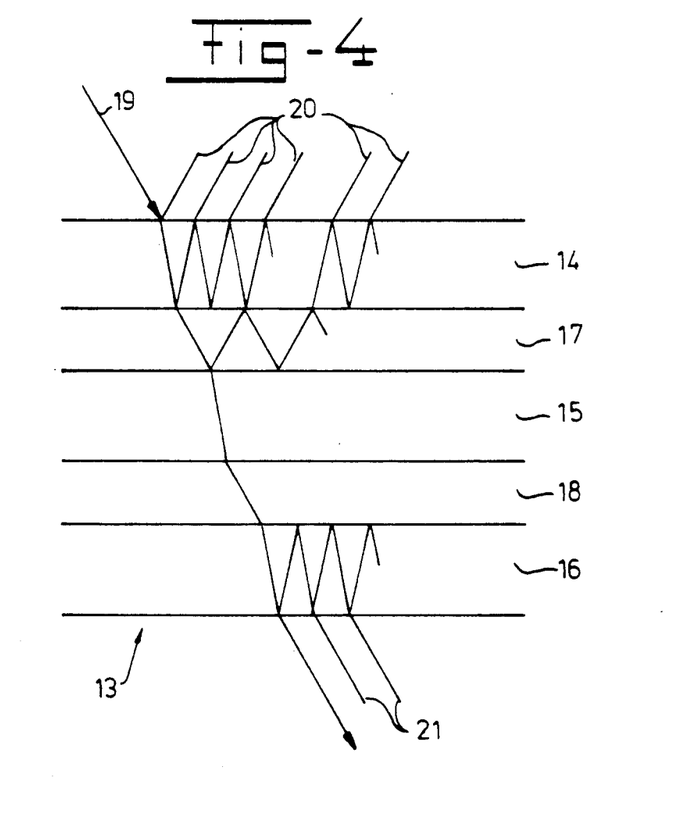
FIG. 4 shows schematically multiple-reflections of ultrasonic signals within the laminate of FIG. 3.

As shown in FIG. 4, an incident ultrasonic pulse 19 gives rise to multiple reflections from and within said laminate 13, which eventually result in reflected signals 20 and/or transmitted signals 21.

From physical considerations, it can be shown that said multiple reflections within the laminate itself, lead to constructive or destructive interferences, dependent on the layer parameters and the wavelength of the incident signal 19.

Figure 5:
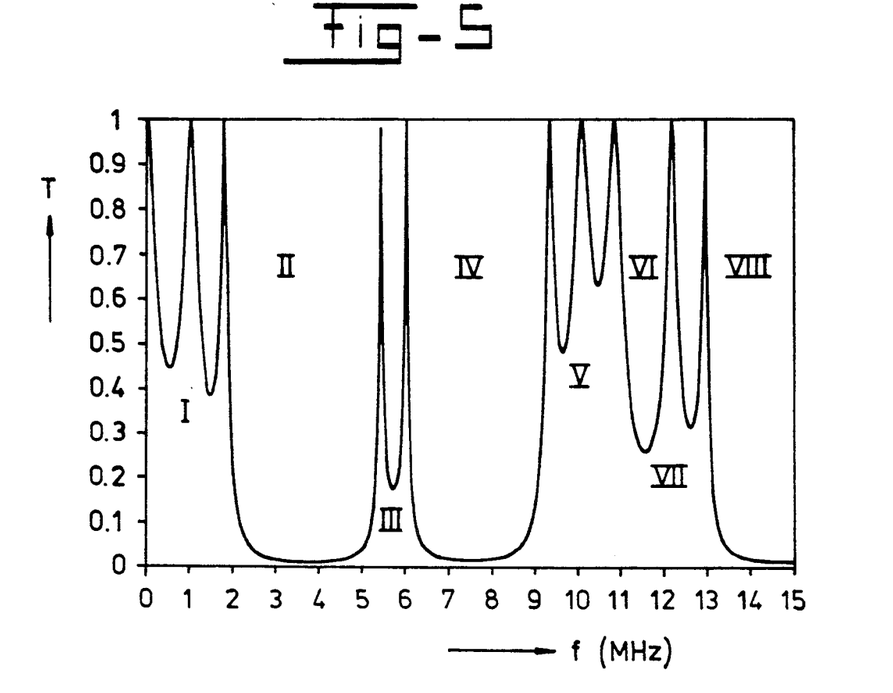
FIG. 5 shows a typical graph of the acoustic frequency behavior of the laminate shown in FIG. 3.

Using a suitable transfer function model, such as described by Brekhovskikh, mentioned above, it can be shown that said laminate has specific transmission frequency bands and specific reflection frequency bands, as graphically illustrated in FIG. 5.

Said graph is calculated for the ARALL laminate shown in FIG. 3, using a computer modelled transfer function according to Brekhovskikh, with an ultrasonic velocity $v_{alu}=6420$ m/s and density $\rho_{alu}=2780$ kg/m$^3$ for the aluminum layers and velocity $v_{ara}=2580$ m/s and density $\rho_{ara}=1330$ kg/m$^3$ for the aramide layers. In said calculated graph, the transmission coefficient T is depicted along the abscissa, whereas in ordinate direction the frequency f is depicted in MHz.

There can be distinguished several acoustic transmission frequency bands, in which non or less reflection occurs, indicated by I, III, V and VII as well as several bands having a strong reflection pattern, i.e. frequency bands II, IV, VI and VIII.

The relatively sharp peaks in the transmission bands relate directly to the number and material of the specific layers of the laminate. The transmission bands I and V are a result of the three aluminum layers, i.e. three peaks, whereas the transmission bands III and VII relate to the two aramide layers, i.e. to peaks in each band. For ARALL laminates having more or less layers, the frequency bands remain nearly the same, except for the number of peaks in the transmission bands.

Figure 6:
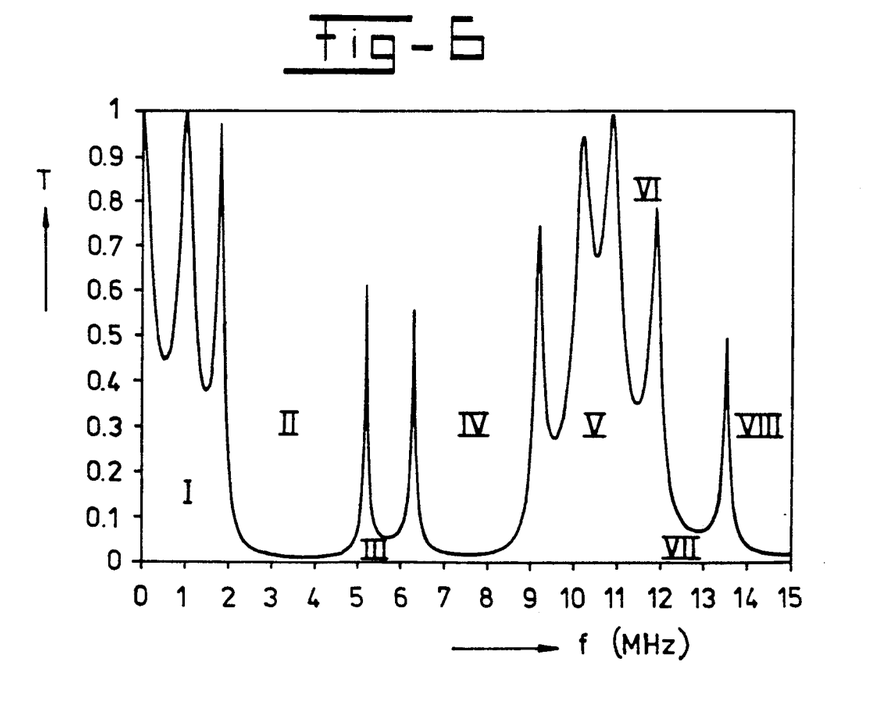
FIG. 6 shows a graph similar as in FIG. 5 obtained from a laminate having the structure as shown in FIG. 3 with mutually different layer thicknesses.

When varying the thicknesses of the individual layers of the ARALL laminate shown in FIG. 3, the frequency characteristics of, for example, FIG. 6 are obtained. This figure is calculated for the laminate 13 having an aramide layer 17 with a thickness of 0.22 mm and an aramide layer 18 having a thickness of 0.18 mm.

By comparing the graphs of FIGS. 5 and 6, it can be seen that the positions of the individual frequency bands remain nearly the same, whereas the height of the peaks in the transmission bands varies strongly for the transmission bands due to the aramide layers, bands III and VII.

It are these variations in the transmission properties of the laminate which might be interpreted as flaws when using a conventional broad-band ultrasonic inspection.

Figure 7:
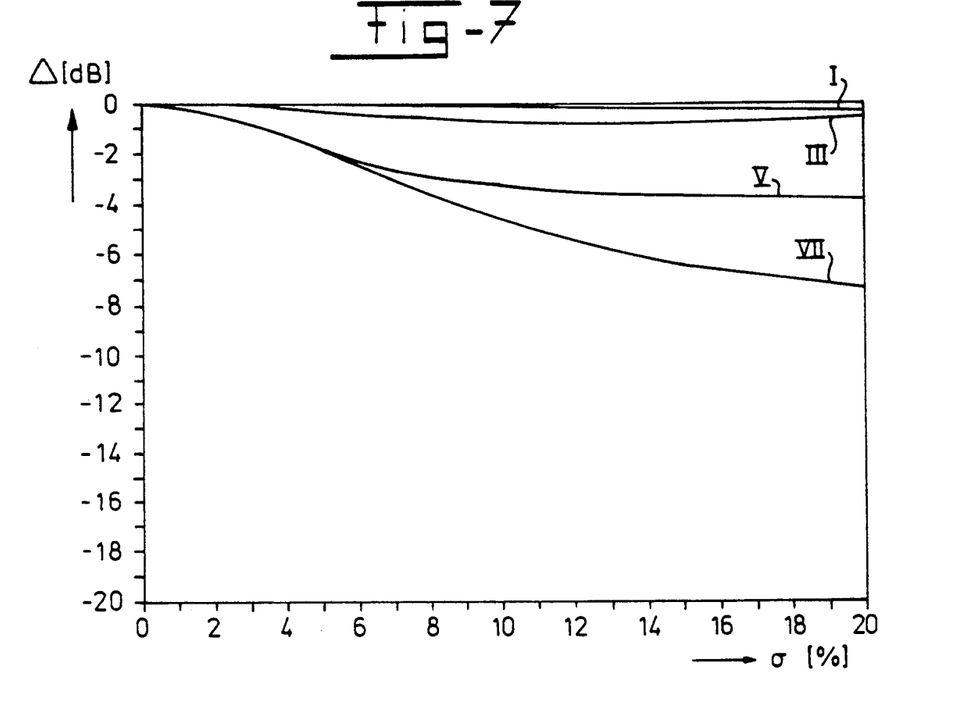
FIG. 7 shows a graph of the transmission loss as function of the deviation in thickness of the fibre layers of the laminate shown in FIG. 3.

FIG. 7 shows the transmission loss $\Delta$ in dB over the standard deviation $\sigma$ in % of the aramide fibre reinforced resin layers 17 and 18 of the laminate shown in FIG. 3. It can be seen that the transmission properties of the transmission bands I and V, relating to the aluminum layers, are neglectably affected compared to the loss in transmission of the fibre layers 17 and 18, i.e. transmission bands III and VII.

In the method according to the invention, influences of these kinds of variations are eliminated by a frequency selective analysis of the structure to be inspected By restricting, for example, the analysis to the transmission bands relating to the aluminum layers in case of ARALL, negligible interferences from variations in fibre layer thicknesses will occur. Accordingly, deviations in transmitted or reflected signals in said transmission bands have to be caused by defects in the laminate.

By counting the peaks in the transmission bands, the number of aluminum and aramide layers of the laminate under inspection can be determined. Further, by comparing the height and position of the individual peaks in a transmission band, information about the thickness variations of the specific layers can be obtained.

Further, by comparatively analyzing the signals within frequency bands, for example the transmission bands I and III or III and V, respectively, signals due to flaws and/or parameter variations can be positively discriminated. Measurements at relatively high frequencies can be necessary because of resolution requirements.

Although only the frequency spectrum variations with respect to the layer thickness of the aramide layers are shown, the transmission and reflection properties of ARALL will, of course, also vary with, for example, the density of the layers or, for example in the case of GLARE, the fibre volume ratio. In practice, variations in the aluminum layers will rarely occur because said layers are not composed during the fabrication of the laminate.

Figure 8:
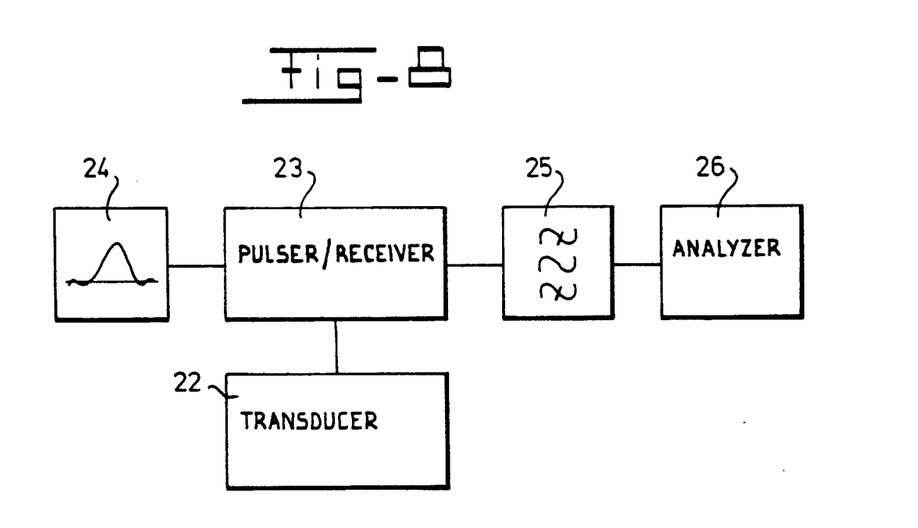
FIG. 8 is a block diagram of an apparatus for carrying out the method according to the invention.

FIG. 8 shows a block diagram of an apparatus for carrying out the method according to the invention. Said apparatus consists of a transducer 22 which receives an electrical pulse from a pulser/receiver unit 23. For shaping the electrical pulse generated by said pulser/receiver unit 23, a pulse shaping unit 24 is provided. For filtering the received reflected signals, a band pass filter unit 25 is provided. Signals from said band pass filter unit 25 are fed to an analyzing unit 26, for analyzing at least one variable of received reflected signals, for example the peak amplitude or energy content of received pulses.

As a result of the electrical excitation of the transducer 22 by the pulser/receiver unit 23, said transducer 22 will vibrate resulting in an ultrasonic signal. This signal travels away from the transducer 22 to the sample to be inspected. The transducer and said sample (not shown) may be immersed in a tank filled with water or squirted by water as a coupling medium, see FIG. 1. In case of the double transmission mode, the signals will be received by the same transducer 22. In the single transmission mode, an other transducer 22 connected to the pulser/receiver unit 22 is provided. Received signals will be amplified by the pulser/receiver unit 23 and analyzed by the analyzing unit 26, which may be a digital analyzing means known as such.

In the block diagram of FIG. 8, both measures according to the invention for obtaining a frequency selective analysis are indicated, i.e. the pulse shaping unit 24 and the (adjustable) band pass filter unit 25. It is, however, optionally to use one or both of said units 24, 25. Using the filter unit 25, a received signal will be band pass filtered before it is analyzed by the analyzing unit 26. By shaping the electrical pulse by the pulse shaping unit 24, for example as a so-called sync function, a pulse having a limited frequency spectrum is obtained. It will be clear that the units 23, 24 and 25, as well as the analyzing unit 26 may be provided as one single apparatus. The transducer can be of a type known in practice for ultrasonic inspection of materials.

Although the invention is explained with reference to ARALL it is of course not limited to such material but can be used for analyzing other multi-layered structures having acoustic transmission and reflection frequency bands.

We claim:

1. A method of ultrasonic inspection of a multi-layered structure having characteristic, ultrasonic transmission and reflection frequency bands related to physical parameters of said multilayer structure, said transmission band frequencies having high transmissivity through said multilayered structure and low reflectivity therefrom and said reflection frequency bands having high reflectivity from said multi-layered structure and low transmissivity therethrough to detect flaws in said structure, said method comprising subjecting said structure to ultrasonic signals, receiving ultrasonic signals modulated by said multi-layer structure, and comparatively analyzing said modulated, ultrasonic signals with respect to said characteristic frequency bands of said structure to distinguish modulating effects due to variations in said physical parameters from modulating effects due to said flaws.

2. A method according to claim 1, wherein the structure is subjected to ultrasonic signals having a frequency spectrum including at least one said transmissivity or reflectivity frequency band of said structure, and wherein said modulated ultrasonic signals are frequency band selective filtered before analyzing.

3. A method according to claim 1, wherein said structure is subjected to ultrasonic signals having a frequency spectrum limited to one specific frequency band of said structure.

4. A method according to claim 1, wherein the transmitted or reflected signals within at least one transmission or reflection frequency band of the structure are analyzed.

5. A method according to claim 1, wherein the transmitted or reflected signals within at least two transmission or reflection frequency bands of the structure relating to different layer materials are comparatively analyzed.

6. A method according to claim 1, wherein peaks in the transmission or reflection frequency bands are analyzed for determining the composition of the structure under inspection.

7. A method according to claim 1, wherein the structure is subjected to ultrasonic pulses, the variable to be analyzed being the peak amplitude and/or the energy content of transmitted or reflected signals in the time domain.

8. A method according to claim 1, wherein the frequency bands of the structure are calculated from the layer thicknesses, the densities of the layer materials and/or the acoustic velocity in each layer, using a computer programmed multi-layered transfer function.

9. A method according to claim 1, wherein several locations of the structure to be inspected are scanned (B-scan; C-scan).

10. A method according to claim 1, wherein the structure to be inspected is ARALL (ARamide ALuminum Laminated) (trademark) or GLARE (trademark).

11. An apparatus for ultrasonic inspection of a multi-layered structure having characteristic, ultrasonic transmission and reflection frequency bands related to physical parameters of said multilayer structure, said transmission band frequencies having high transmissivity through said multilayered structure and low reflectivity therefrom and said reflection frequency bands having high reflectivity from said multi-layered structure and low transmissivity therethrough to detect flaws in said structure, said apparatus comprising a transducer for emitting ultrasonic signals to said structure and for receiving signals modulated by said structure, means for comparatively analyzing at least one variable of said modulated signals to distinguish modulating effects due to variations in said physical parameters from modulating effects due to said flaws, and filter means adapted to at least one frequency band of said structure, for filtering transmitted or reflected ultrasonic signals.

12. An apparatus according to claim 11, wherein the signals are ultrasonic pulses, and the means for analyzing the transmitted or reflected signals comprise means for measuring the peak amplitude of transmitted or reflected signals in the time domain.

13. An apparatus according to claim 11, wherein the signals are ultrasonic pulses, and the means for analyzing the transmitted or reflected signals comprise means for measuring the energy content of transmitted or reflected signals in the time domain.

14. An apparatus according to claim 11, comprising comparator means for comparing transmitted or reflected signals within several frequency bands of the structure under inspection.

15. An apparatus according to claim 11, comprising means for scanning several locations of the structure to be inspected (B-scan; C-scan).

16. An apparatus for ultrasonic inspection of a multi-layered structure having characteristic, ultrasonic transmission and reflection frequency bands related to physical parameters of said multilayer structure, said transmission band frequencies having high transmissivity through said multilayered structure and low reflectivity therefrom and said reflection frequency bands having high reflectivity from said multi-layered structure and low transmissivity therethrough to detect flaws in said structure, said apparatus comprising a transducer for emitting ultrasonic signals to said structure and for receiving signals modulated by said structure, means for comparatively analyzing at least one variable of said modulated signals to distinguish modulating effects due to variations in said physical parameters from modulating effects due to said flaws, and means for emitting ultrasonic signals having a frequency spectrum adapted to a frequency band of said structure.

17. An apparatus according to claim 16, wherein the signals are ultrasonic pulses, and the means for analyzing the transmitted or reflected signals comprise means for measuring the peak amplitude of transmitted or reflected signals in the time domain.

18. An apparatus according to claim 16, wherein the signals are ultrasonic pulses, and the means for analyzing the transmitted or reflected signals comprise means for measuring the energy content of transmitted or reflected signals in the time domain.

19. An apparatus according to claim 16, comprising comparator means for comparing transmitted or reflected signals within several frequency bands of the structure under inspection.

20. An apparatus according to claim 16, comprising means for scanning several locations of the structure to be inspected (B-scan; C-scan).

* * * * *